(12) United States Patent
Walther et al.

(10) Patent No.: US 9,737,654 B2
(45) Date of Patent: Aug. 22, 2017

(54) INTRAVENOUS POLE BASE HAVING TESSELLATING ELEMENTS

(71) Applicant: Medline Industries, Inc., Northfield, IL (US)

(72) Inventors: Linda M. Walther, Pleasant Prairie, WI (US); Frank Martorelli, Hoffman Estates, IL (US); Cristobal J. Rodriguez, Elgin, IL (US)

(73) Assignee: Medline Industries, Inc., Northfield, IL (US)

( * ) Notice: Subject to any disclaimer, the term of this patent is extended or adjusted under 35 U.S.C. 154(b) by 0 days.

(21) Appl. No.: 15/430,117

(22) Filed: Feb. 10, 2017

(65) Prior Publication Data

US 2017/0151386 A1    Jun. 1, 2017

Related U.S. Application Data

(63) Continuation-in-part of application No. 13/339,788, filed on Dec. 29, 2011.
(Continued)

(51) Int. Cl.
*F16M 13/00* (2006.01)
*A61M 5/14* (2006.01)
(Continued)

(52) U.S. Cl.
CPC .......... *A61M 5/1415* (2013.01); *F16M 11/22* (2013.01); *F16M 11/42* (2013.01);
(Continued)

(58) Field of Classification Search
CPC .............. A61M 5/1415; A61M 5/1413; A61M 5/1417; A61M 2209/082; A61M 5/1414;
(Continued)

(56) References Cited

U.S. PATENT DOCUMENTS

| | | | | |
|---|---|---|---|---|
| 1,893,799 A | * | 1/1933 | Harrincton | B01L 9/00 |
| | | | | 248/188.7 |
| 3,188,033 A | * | 6/1965 | Groves | A47C 7/004 |
| | | | | 248/188.7 |

(Continued)

OTHER PUBLICATIONS

SmartStack Basic I.V. Stand data sheet. Retrieved from Maxtec website, www.maxtecinc.om. We know this information to have been publicly available via the Internet at least as early as Dec. 29, 2010.

*Primary Examiner* — Brian Mattei
*Assistant Examiner* — Taylor Morris
(74) *Attorney, Agent, or Firm* — Fitch, Even, Tabin & Flannery LLP

(57) ABSTRACT

An IV pole base is configured to couple in a tessellating manner to at least one other like IV pole base. The IV pole base can comprise a horizontal rectangular plate having four side edges and a given thickness (at least along the aforementioned side edges). This plate has a plurality of tessellating elements comprising each of a blank and a tab formed at each of the four side edges. The IV pole base further comprises a stabilizing thickening element disposed at a periphery of at least one of the tessellating elements to locally increase the thickness of the IV pole base beyond the thickness of the plate to thereby increase tessellation stability. The plate also includes an IV pole coupler formed centrally thereto, the IV pole coupler being configured to receive and hold an IV pole such that the IV pole extends outwardly perpendicularly to the plate.

18 Claims, 4 Drawing Sheets

Related U.S. Application Data

(60) Provisional application No. 62/446,964, filed on Jan. 17, 2017.

(51) Int. Cl.

| | |
|---|---|
| *F16M 11/42* | (2006.01) |
| *F16M 11/22* | (2006.01) |
| *F16M 13/02* | (2006.01) |
| *F16L 3/00* | (2006.01) |
| *A47F 5/00* | (2006.01) |
| *A47F 7/00* | (2006.01) |
| *F16M 11/00* | (2006.01) |
| *A47K 1/04* | (2006.01) |
| *A47B 91/00* | (2006.01) |
| *A47G 29/00* | (2006.01) |
| *B65D 19/00* | (2006.01) |
| *A47C 21/00* | (2006.01) |
| *A47C 31/00* | (2006.01) |
| *F16D 1/00* | (2006.01) |
| *F16M 11/20* | (2006.01) |
| *A61G 7/05* | (2006.01) |

(52) U.S. Cl.
CPC .......... *F16M 13/02* (2013.01); *A61G 7/0503* (2013.01); *A61G 2203/80* (2013.01); *A61M 5/1413* (2013.01); *A61M 5/1414* (2013.01); *A61M 5/1417* (2013.01); *A61M 2209/082* (2013.01); *A61M 2209/084* (2013.01); *F16M 11/20* (2013.01)

(58) Field of Classification Search
CPC ......... A61M 2209/084; A61G 2203/80; A61G 7/0503; F16M 11/20; F16M 11/22; F16M 11/42
USPC ........... 248/121, 125.8, 129, 346.01, 346.03, 248/346.11, 519; 5/503.1; 211/85.13; 403/381
See application file for complete search history.

(56) References Cited

U.S. PATENT DOCUMENTS

| | | | | |
|---|---|---|---|---|
| 4,511,157 A | * | 4/1985 | Wilt, Jr. ................... | A61G 5/10 280/304.1 |
| 4,511,158 A | * | 4/1985 | Varga ....................... | A61G 7/05 248/229.11 |
| 4,564,732 A | * | 1/1986 | Lancaster ................ | B41J 5/105 200/293 |
| 4,807,412 A | * | 2/1989 | Frederiksen ....... | A47G 27/0212 52/177 |
| 5,125,607 A | * | 6/1992 | Pryor ................. | A61M 5/1415 248/125.1 |
| 5,431,509 A | * | 7/1995 | Anderson ........... | A61M 5/1413 248/225.11 |
| 5,533,697 A | | 7/1996 | Fletcher | |
| 6,032,590 A | * | 3/2000 | Chen ....................... | A47B 3/06 108/158.12 |
| 6,179,260 B1 | * | 1/2001 | Ohanian ................. | A61G 7/05 248/219.4 |
| 7,014,384 B2 | * | 3/2006 | Nicoletti .............. | A47B 87/002 403/192 |
| 7,833,077 B1 | | 11/2010 | Simmons, Jr. | |
| 2004/0011941 A1 | | 1/2004 | Roepke | |
| 2008/0234116 A1 | * | 9/2008 | Elzerman ............. | A63B 21/015 482/123 |
| 2008/0296443 A1 | | 12/2008 | Lunitz | |
| 2009/0146027 A1 | | 6/2009 | Zitting | |
| 2010/0043334 A1 | * | 2/2010 | Rodriguez Alcaine ................ | E04F 15/022 52/588.1 |
| 2011/0240806 A1 | | 10/2011 | Crager | |
| 2012/0223479 A1 | * | 9/2012 | Pabon ....................... | A63F 3/02 273/236 |
| 2014/0361129 A1 | * | 12/2014 | Gomez ............... | A61M 5/1415 248/146 |
| 2016/0270530 A1 | * | 9/2016 | Heyring ................. | A47B 91/16 |

* cited by examiner

INTRAVENOUS POLE BASE HAVING TESSELLATING ELEMENTS

RELATED APPLICATION(S)

This application claims benefit of U.S. Provisional Application No. 62/446,964, filed Jan. 17, 2017 and this application is a continuation-in-part of co-pending and co-owned U.S. patent application Ser. No. 13/339,788, entitled APPARATUS PERTAINING TO A BASE FOR A VERTICAL SUPPORT POLE and filed Dec. 29, 2011, which is incorporated by reference in its entirety herein.

TECHNICAL FIELD

This invention relates generally to intravenous poles.

BACKGROUND

Intravenous (IV) poles and bases for such poles are known in the art. IV pole bases typically comprise a base that supports a vertically-disposed IV pole. The IV pole, in turn, typically has arms, hooks, or other features upon which medical-services providers can hang, for example, bags of intravenous fluids, medications, and various electro-mechanical apparatuses. IV poles are typically provided in considerable numbers at medical-services facilities such as hospitals, urgent care centers, nursing homes, rehabilitation centers, and so forth.

IV poles and their bases are typically, by design, portable. Many IV pole bases have casters or other rollers to facilitate moving the IV pole from place to place. This portability well suits the ordinary use of such an apparatus in a service-care environment. For any number of reasons it may be convenient or even essential that a given IV pole be moved from one place to another. As one simple example in these regards, a single IV pole may move as a corresponding patient moves from a pre-operation staging area to the operating room and then to a recovery area. As another example, many medical-services facilities require that all IV poles and their bases be taken from time to time to a cleaning/sanitizing area for cleaning/sanitizing.

Unfortunately, while many IV poles are designed to be easily moved on their bases (for example, by rolling), most are only designed to be moved in isolation. This can make it difficult for a maintenance person to simultaneously move a relatively large number of IV poles (such as, for example, four, six, or a dozen) from one place to another. In some cases the IV pole bases have vertical legs and maintenance personnel stack or otherwise intertwine those legs to attempt make it easier to move a plurality of such poles at the same time. That said, this intertwining of vertical elements can yield uncertain connections, can be challenging to untwine, and can even raise the center of gravity for the intertwined poles and thereby make it easier for the poles to topple during movement. Such intertwining can also lead to marring or otherwise damaging the surface treatment of the base.

BRIEF DESCRIPTION OF THE DRAWINGS

The above needs are at least partially met through provision of the intravenous pole base having tessellating elements described in the following detailed description, particularly when studied in conjunction with the drawings, wherein.

Figure 1:
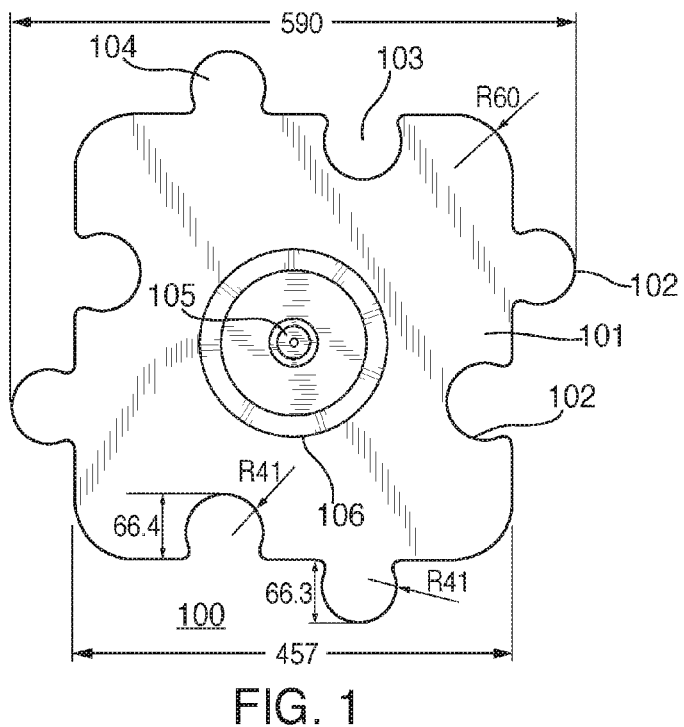
FIG. 1 comprises a top plan view as configured in accordance with various embodiments of the invention.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments of the present invention. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, pursuant to these various embodiments an IV pole base is configured to couple in a tessellating manner to at least one other like IV pole base. The IV pole base can comprise a horizontal rectangular plate having four side edges and a given thickness (at least along the aforementioned side edges). This plate has a plurality of tessellating elements comprising each of a blank and a tab formed at each of the four side edges. The IV pole base further comprises a stabilizing thickening element disposed at a periphery of at least one of the tessellating elements to locally increase the thickness of the IV pole base beyond the thickness of the plate to thereby increase tessellation stability. The plate also includes an IV pole coupler formed centrally thereto, the IV pole coupler being configured to receive and hold an IV pole such that the IV pole extends outwardly perpendicularly to the plate.

The aforementioned plate can be comprised of any of a variety of materials. Generally speaking, both weight and strength are beneficial and accordingly the plate can be comprised of steel or the like.

By one approach, the aforementioned blanks and tabs each have a substantially circular shape. Since these elements are configured to have a tessellating relationship, the sizes of the blanks and tabs are close but not exactly of the same size. Instead, the tabs are slightly smaller than the blanks to permit the tabs to be readily placed within (and removed from) the blanks but without much play or opportunity for lateral movement once so placed.

The aforementioned stabilizing thickening element can be comprised of a hard plastic material and by one approach each of the tessellating elements can be provided with one of the stabilizing thickening elements. Generally speaking, by one approach the outer edge of the stabilizing thickening element corresponds to the periphery of the corresponding tessellating element. When the tessellating elements have a circular shape, accordingly, the stabilizing thickening elements can have, for example, a truncated ring shape. By one approach each stabilizing thickening element has a thickness at least equal to the thickness of the plate.

So configured, these stabilizing thickening elements serve to "thicken" the relative thickness of the tessellating elements beyond the thickness of the plate itself. When one such IV pole base is coupled in a tessellating matter to another like IV pole base, these stabilizing thickening elements serve to "stabilize" that tessellating coupling by helping to preserve that tessellating coupling when moving joined IV pole bases. For example, such an arrangement can be rolled over a disruption or discontinuity in the floor surface sufficient to cause dynamic variations in the height of one of the IV pole bases relative to another of the IV pole bases without permitting the respective tessellating elements to become uncoupled from one another.

To facilitate ease of movement, by one approach the plate can have a plurality of rolling members (such as casters) coupled to an underside thereof.

By one approach, these IV pole bases can be provided in a plurality of colors. This color coding can facilitate easily returning the IV poles to their primary-use stations. For example, green bases can correlate to an emergency-services area while blue bases can belong to a maternity wing.

So configured, a large number of IV pole bases and their corresponding IV poles can be easily, quickly, and securely attached to one another to facilitate moving those poles, as a group, from place to place. These IV pole bases can just as easily be disconnected from one another. By interlocking at a same vertical level from one base to the next, the center of gravity remains constant and helps to avoid toppling the IV poles during movement. These teachings are readily and economically applied with respect to a variety of existing IV pole designs and hence can serve to leverage the continued viability of those existing designs. These teachings are also highly scalable and will work with a wide variety of vertical support poles.

Figure 2:
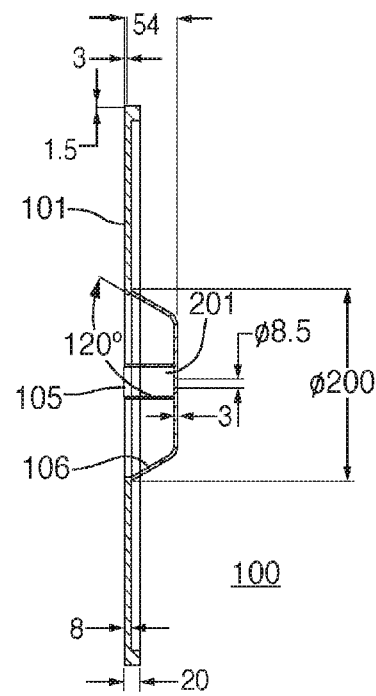
FIG. 2 comprises a side-elevational sectioned view as configured in accordance with various embodiments of the invention.
Figure 3:
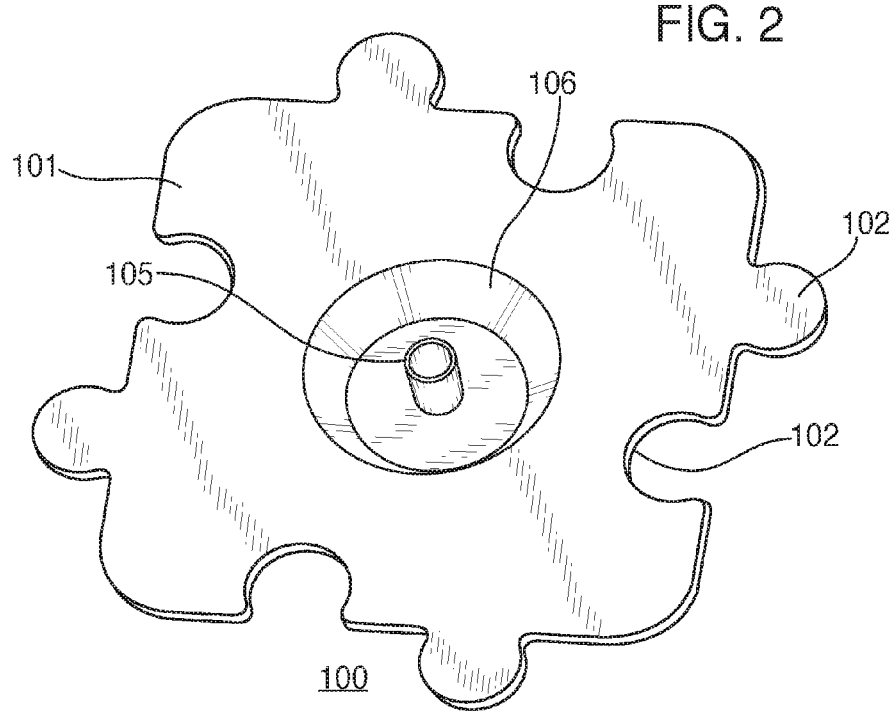
FIG. 3 comprises a top perspective view as configured in accordance with various embodiments of the invention.

These and other benefits may become clearer upon making a thorough review and study of the following detailed description. Referring now to the drawings, and in particular to FIGS. 1, 2 and 3, an illustrative apparatus that is compatible with many of these teachings will be presented.

In this illustrative example the IV pole base 100 comprises a plate 101 having a generally rectangular shape albeit with rounded corners. More particularly, in this example the plate 101 is square-shaped. Other shapes are possible, of course, including a variety of rectangles as well as other regular and irregular shapes. The relative dimensions of the plate 101 can vary with the needs of a given application setting. In this example the plate 101 comprises a horizontal plate in that the plate 101 is both planar and configured to be disposed horizontally during ordinary use when supporting a corresponding IV pole in an application setting such as a hospital, urgent care facility, nursing home, or the like.

The plate 101 can be sized as desired. Here, a number of useful suggested dimensions (expressed as millimeters) are shown in FIGS. 1 and 2. It will be understood that these particular dimensions are provided for the sake of a useful illustrative example and are not intended to express any required or essential absolute or relative dimensions.

This plate 101 can be comprised of any of a variety of materials. Examples include, but are not limited to, any of a variety of plastics or metals to natural materials such as wood. By one approach, and as presumed here for the purposes of this description, the plate 101 comprises steel such as, but not limited to, Q195 grade of steel.

This plate 101 has a plurality of tessellating elements 102 formed along its side edges. In this particular example each of the side edges of the plate 101 has two such tessellating elements 102. These tessellating elements 102 comprise so-called blanks and tabs. A "blank" comprises an opening 103 into the plate 101 whereas a "tab" comprises an extension 104 away from the plate 101. In this illustrative example the blanks and tabs are complimentary to one another. This means that the tabs have a shape and size that is essentially the same as the shape and size of the blanks though slightly smaller as compared thereto.

The blanks/tabs can have whatever shape may be desired. As pictured, and as one illustrative example in these regards, these tessellating elements 102 can have a substantially circular shape (where "substantially" as used in this context means at least fifty percent). That said, and again, other shapes can be readily accommodated. Generally speaking, the shape and size of the tessellating elements 102 should be such that two such plates 101 are physically interlocked with one another when the tab of one such plate 101 is tessellated with a corresponding and complimentary blank of another such plate 101.

With continued reference to FIGS. 1 through 3, in this illustrative example the plate 101 also includes an IV pole coupler 105 formed central to the plate 101. This IV pole coupler 105 is configured to receive and hold an IV pole such that the IV pole extends outwardly perpendicularly to the plate 101 (and, more particularly, upwardly from the plate 101). In this example the IV pole coupler 105 comprises a tube sized and shaped to receive the base of a typical IV pole. As perhaps best shown in FIG. 2, the plate 101 has a hole 201 disposed therethrough to receive a bolt that serves to secure the IV pole to the IV pole coupler 105.

Also shown in this illustrative example is a cup 106 formed in the plate 101 such that the IV pole coupler 105 is centrally disposed within the cup 106 and rises upwardly from the bottom of the cup 106. The cup 106 extends below the majority of the bottom surface of the plate 101 and hence serves to lower the effective center of gravity of the apparatus, particularly when connected to an IV pole. Accordingly, this configuration can help to maintain the vertical stability of the apparatus and thereby help to prevent the apparatus from falling over, either during use or when being moved.

By one approach this cup 106 has sidewalls that are vertically aligned. By another approach, and as illustrated, the sidewalls of the cup 106 can be inclined inwardly towards the bottom of the cup 106. Inclined walls can help facilitate cleaning the cup 106 during ordinary maintenance of the IV pole base 100.

Figure 4:
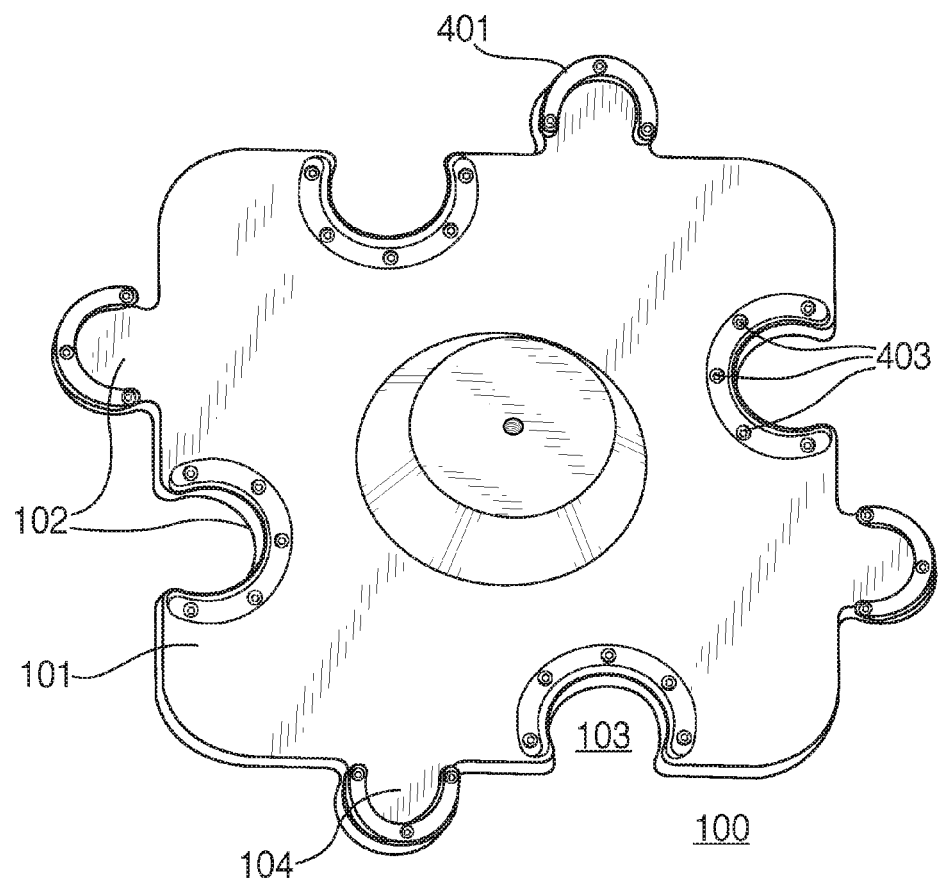
FIG. 4 comprises a bottom perspective view as configured in accordance with various embodiments of the invention.
Figure 5:
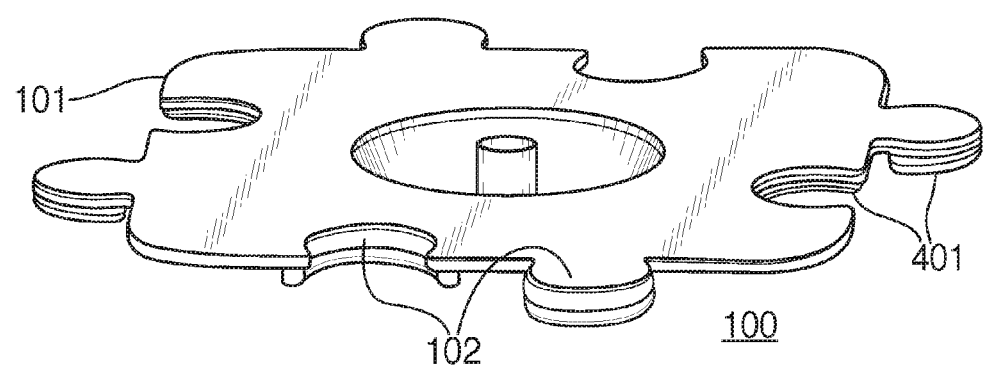
FIG. 5 comprises a side perspective view as configured in accordance with various embodiments of the invention.

Referring now to FIGS. 4 and 5, the aforementioned tessellating elements 102 can have stabilizing thickening elements 401 disposed at the peripheries thereof. By one approach only one of the tessellating elements 102 has a stabilizing thickening element 401. These teachings will accommodate, however, providing each of the tessellating elements 102 with a stabilizing thickening element 401. As illustrated, all of the tessellating elements 102 each have a stabilizing thickening element 401. Generally speaking, each such stabilizing thickening element 401 is disposed at the outer periphery of a corresponding one of the tessellating elements 102 to thereby locally increase the thickness of the IV pole base 100 beyond the thickness of the plate 101 to thereby increase tessellating stability.

In this example all of the stabilizing thickening elements 401 are disposed on the underside surface of the plate 101 and are attached to the plate 101 by threaded members 403 (such as, for example bolts). Other securement mechanisms can be employed if desired. Generally speaking an adhesive may not serve well in these regards because regular cleaning of the IV pole bases 100 may include use of a pressure washer. If desired, some or all of the stabilizing thickening elements 401 may be secured instead to the upper side of the plate 101. These teachings will also accommodate placing stabilizing thickening elements 401 on both the underside and the upper side of the plate 101. For many application settings, however, it will likely be preferable to dispose the stabilizing thickening elements 401 on the underside of the plate 101 as shown as such a configuration will tend to facilitate rather than hinder engaging one tessellating element with another.

By one approach the entire underside, at or least some large majority portion thereof, can have a single stabilizing thickening element 401 attached thereto, the stabilizing thickening element 401 being of sufficient size and extent to be coextensive with a periphery of each of the tessellating elements 102. By another approach, a one-piece stabilizing thickening element 401 can comprise a relatively narrow piece that extends conformally about the periphery of the plate 101, including the tessellating elements 102, somewhat in the manner of a ring-shaped gasket. (As used herein, the word "conformally" shall be understood to mean to conform to a given shape by matching that shape in a coextensive manner.) Generally speaking, however, it will be both sufficient and economical to employ a plurality of smaller stabilizing thickening elements 401, one per tessellating element 102, as illustrated.

In this example, where the tessellating elements 104 have a circular form factor, the stabilizing thickening elements 401 can themselves each have a truncated ring shape. That said, the stabilizing thickening elements 401 can each be shaped to be conformally disposed along at least a majority portion (and preferably along at least seventy or eighty percent) of the periphery of the corresponding tessellating element 401.

The stabilizing thickening elements 401 can all have an equal thickness or can have varied thicknesses if desired. By one approach the stabilizing thickening elements 401 have a thickness that is at least equal to the thickness of the plate 101. These teachings will readily accommodate, however, using stabilizing thickening elements 401 that are thicker than the plate 101. For the purposes of this description it is presumed that the stabilizing thickening elements 401 have a thickness of 15 mm. As well illustrated in FIG. 5, these stabilizing thickening elements 401 can be disposed coextensive with the periphery of the corresponding tessellating elements 102 and thereby serve to considerable increase the relative thickness of the edge of the IV pole base 100 at the edges of the tessellating elements 102.

The stabilizing thickening elements 401 can be comprised of any suitable material. By one approach, for example, the stabilizing thickening elements 401 are formed of a metal, either the same as the plate 101 or a different metal. Generally speaking, however, it will likely be preferable that the stabilizing thickening elements 401 are formed of a hard plastic material such as, for example a polyamide (PA) plastic. The material should be hard/resilient enough to avoid being unduly deformed or dinged during ordinarily usage but light enough to avoid unduly increasing the weight of the IV pole base 100.

Figure 6:
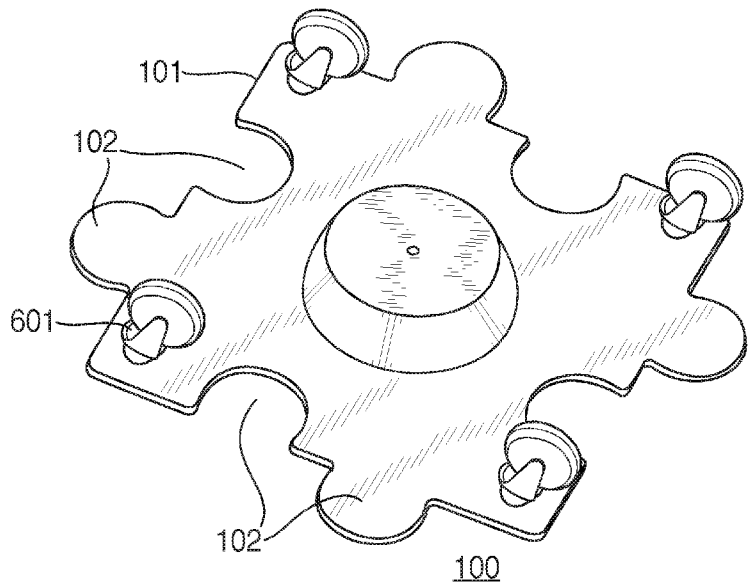
FIG. 6 comprises a bottom perspective view as configured in accordance with various embodiments of the invention.

To facilitate the aforementioned horizontal movement, and as shown in FIG. 6, the IV pole base 100 can include one or more rolling elements attached to the plate 101. By way of illustration and without intending any limitations in these regards, this can comprise attaching a plurality of caster assemblies 601 (such as standard three-inch casters) to the underside of the plate 101. Though other wheeled components can serve in these regards, casters can be particularly useful as casters can rotate about a support shaft. This, in turn, permits casters to facilitate ease of movement in essentially any direction. In this illustrative example the plate 101 has one such caster assembly 601 disposed in each corner of the square that comprises the plate 101. (For the sake of clarity and simplicity, the aforementioned stabilizing thickening elements 401 are not shown in FIG. 6.)

Figure 7:
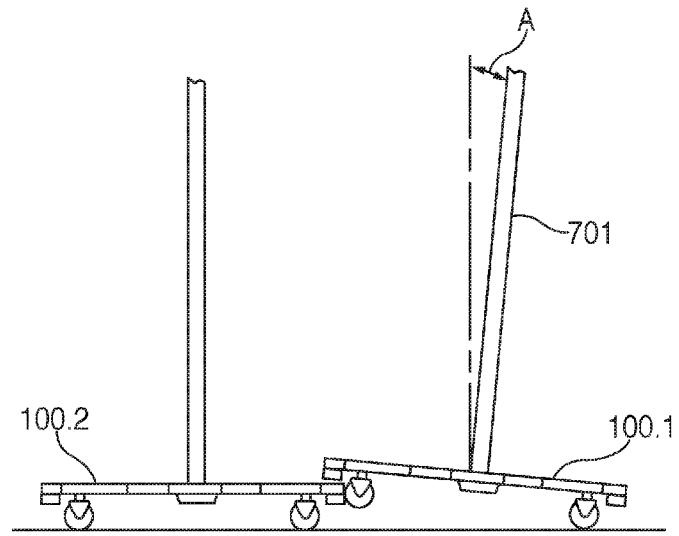
FIG. 7 comprise a side elevational view as configured in accordance with various embodiments of the invention.

With reference to FIG. 7, a first such IV pole base 100.1 can be physically coupled to another such IV pole base 100.2 in a tessellating manner by tilting the first IV pole base 100.1 at least some required angle with respect to the horizontal rectangular plate 101 of the second IV pole base 100.2 (shown here as the corresponding angle "A" by which the IV pole 701 for the first IV pole base 100.1 is tilted with respect to the vertical axis). For the dimensions shown in FIGS. 1 and 2, and presuming the use of three-inch casters, this angle A is about 6 degrees. (It would also be possible, of course, to vertically lift one of the IV pole bases 100, properly position that IV pole base 100 over the other by aligning the corresponding tessellating elements 102, and then lowering that IV pole base 100 straight down to engage those tessellating elements 102; at least because the IV pole base can weigh around thirty pounds, however, the tilted approach described above can represent the less-strenuous approach.)

Figure 8:
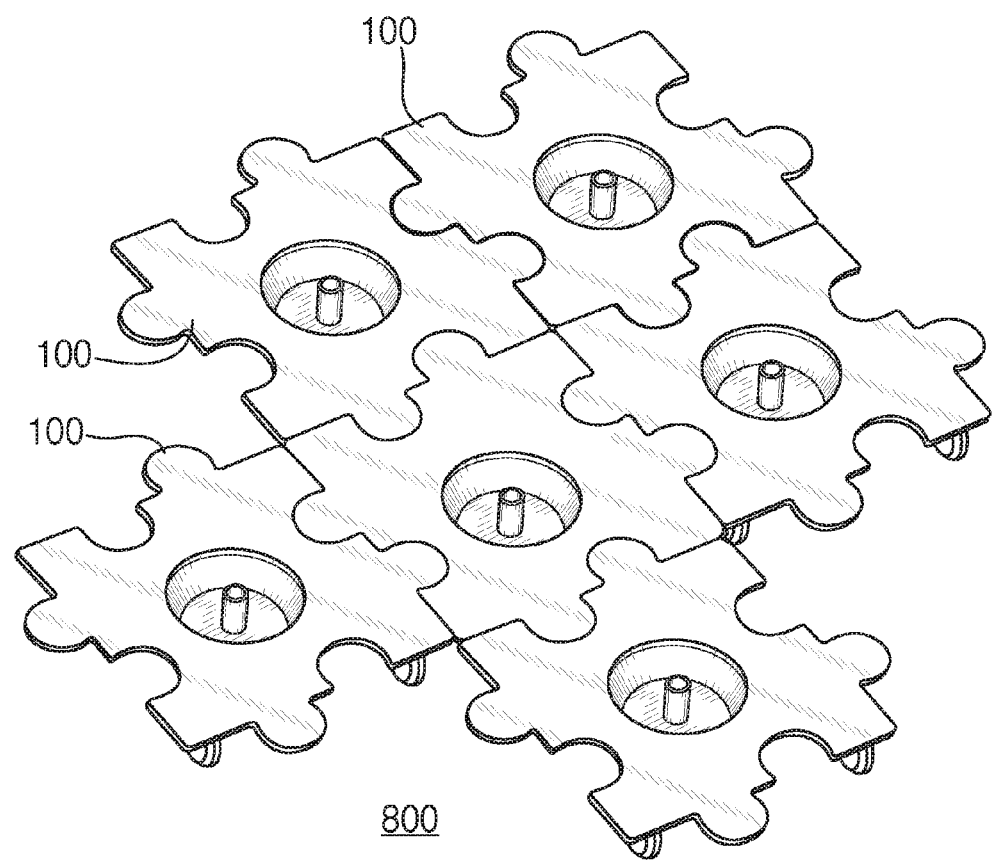
FIG. 8 comprises a top perspective view as configured in accordance with various embodiments of the invention.

FIG. 8 provides a further illustrative example in these regards. In this example six such IV pole bases 100 are interlocked one to the other by tessellating their respective tabs and blanks as described above. (For the sake of clarity these IV pole bases 100 are shown without the aforementioned stabilizing thickening elements 401 and without any IV poles 701.) In this particular example these IV pole bases 100 interlock with one another like jigsaw-puzzle pieces in a tessellated manner such that adjacent IV pole bases 100 are juxtaposed one to the other without substantial overlap or gaps.

Being interlocked in this manner, horizontally moving one of the IV pole bases 100 (for example, across a floor) will cause the remaining IV pole bases 100 to move horizontally as well; as one IV pole base 100 moves so move the remaining IV pole bases 100. A maintenance person can easily attach additional IV pole bases 100 and can readily move the attached IV pole bases 100 from place to place as desired. These IV pole bases 100 can also be easily disconnected from one another (for example, by again tilting one of the IV pole bases 100 as described above to de-tessellate the engaged tessellating elements 102) as desired to thereby singulate one or more of the IV pole bases 100.

There are no strict limits as to how many IV pole bases 100 can be joined in this manner into a single assembly. It will also be noted that the IV pole bases 100 can all be joined in a single line or with at least some IV pole bases 100 interconnected to the sides of such a collection (as shown).

By one approach at least some of these IV pole bases 100 can be color coded. Yellow bases, for example, can correspond to a first area of a given facility while red bases can correspond to a second, different area of that facility. The use of such color coding can facilitate identifying IV poles that should be moved to a different location as well as the particular destination to which the IV pole should be moved. These teachings will accommodate using other identifiers as well if desired, such as text or graphic elements such as representative icons or the like.

So configured, a plurality of IV pole bases 100 can be easily connected and disconnected from one another to permit and facilitate moving a plurality of such apparatuses from one location to another. The secure tessellated interlock (made considerably more secure by use of the aforementioned stabilizing thickening elements 102) ensures that the IV pole bases 100 remain connected to one another while moving an aggregation of such IV pole bases 100, even when moving over small perturbations and gaps in the floor such as the gap and possible difference in height that occurs between a building floor and an elevator floor.

It will also be appreciated that the described approaches can be economically realized and can also be used with existing IV poles to improve the continued use and viability of those poles.

Those skilled in the art will recognize that a wide variety of modifications, alterations, and combinations can be made with respect to the above described embodiments without departing from the spirit and scope of the invention, and that such modifications, alterations, and combinations are to be viewed as being within the ambit of the inventive concept.

We claim:

1. An intravenous (IV) pole base configured to couple in a tessellating manner to at least one other like IV pole base comprising:
   a horizontal rectangular plate having four side edges and a thickness, the plate further having a plurality of tessellating elements comprising each of a blank and a tab formed at each of the four side edges;
   a stabilizing thickening element disposed at a periphery of at least one of the tessellating elements to locally increase thickness of the IV pole base beyond the thickness of the plate and thereby increase tessellation stability;
   an IV pole coupler formed central to the plate and configured to receive and hold an IV pole such that the IV pole extends outwardly perpendicularly to the plate.

2. The IV pole base of claim 1 wherein the plate is comprised of a first material and the tessellating elements are comprised of a second, different material.

3. The IV pole base of claim 2 wherein the first material comprises a metal and the second material comprises a plastic.

4. The IV pole base of claim 3 wherein the metal comprises steel.

5. The IV pole base of claim 1 wherein all of the tessellating elements include the stabilizing thickening element disposed at their peripheries.

6. The IV pole base of claim 5 wherein the stabilizing thickening elements are disposed on an underside surface of the plate.

7. The IV pole base of claim 6 wherein the stabilizing thickening elements are attached to the plate by threaded members.

8. The IV pole base of claim 5 wherein the stabilizing thickening elements are each conformally disposed along at least a majority portion of the periphery of each of the tessellating elements.

9. The IV pole base of claim 8 wherein the stabilizing thickening elements are at least equal to the thickness of the plate.

10. The IV pole base of claim 9 wherein the stabilizing thickening elements are thicker than the thickness of the plate.

11. The IV pole base of claim 5 wherein the stabilizing thickening elements each have a truncated ring shape.

12. The IV pole base of claim 5 wherein the plate has a cup formed therein that includes the IV pole coupler.

13. The IV pole base of claim 12 wherein the cup extends below a bottom surface of the plate.

14. The IV pole base of claim 12 wherein the cup has inclined cup walls.

15. The IV pole base of claim 5 further comprising:
    a plurality of rolling members disposed on an underside of the plate.

16. The IV pole base of claim 15 wherein the rolling members comprise casters.

17. The IV pole base of claim 5 wherein each of the tessellating elements has a circular shape.

18. The IV pole base of claim 1 wherein the IV pole base is configured to partially overlay the other like IV pole base to thereby facilitate engaging the tessellating elements of both IV pole bases by tilting the horizontal rectangular plate by at least 6 degrees with respect to the horizontal rectangular plate of the other like IV pole base.

* * * * *